US006192751B1

United States Patent
Stein et al.

(10) Patent No.: US 6,192,751 B1
(45) Date of Patent: Feb. 27, 2001

(54) NON-INVASIVE LOW FREQUENCY ELASTIC WAVE FLUID LEVEL SENSING SYSTEM FOR SLUDGE LADEN ENVIRONMENTS

(75) Inventors: Peter J. Stein, Hollis; Steven Edmund Euerle, Nahsua, both of NH (US)

(73) Assignee: Scientific Solutions, Inc., Hollis, NH (US)

( * ) Notice: Subject to any disclaimer, the term of this patent is extended or adjusted under 35 U.S.C. 154(b) by 0 days.

(21) Appl. No.: 08/972,517

(22) Filed: Nov. 18, 1997

(51) Int. Cl.$^7$ .................................................. G08B 21/00
(52) U.S. Cl. ..................................... 73/290 V; 73/861.18; 73/61.79; 340/617; 340/621
(58) Field of Search .................................... 73/290 V, 597, 73/61.79, 64.53, 861.18; 340/617, 621

(56) References Cited

U.S. PATENT DOCUMENTS

| | | | | |
|---|---|---|---|---|
| 4,213,337 | * | 7/1980 | Langdon | 73/290 |
| 4,954,997 | * | 9/1990 | Dieulesaint et al. | 367/13 |
| 5,015,995 | * | 5/1991 | Holroyd | 340/621 |
| 5,456,114 | | 10/1995 | Liu et al. . | |
| 5,533,389 | * | 7/1996 | Kamen et al. | 73/149 |

OTHER PUBLICATIONS

Langdon, Nov. 1981, "Vibratory process control transducers", Electronic Engineering vol. 53, pp. 159–168.*

* cited by examiner

*Primary Examiner*—Hezron Williams
*Assistant Examiner*—Michael Cygan
(74) *Attorney, Agent, or Firm*—Davis and Bujold

(57) ABSTRACT

A non-invasive elastic wave fluid level sensing system for use in sludge laden environments, including transmitting and receiving transducers mounted on an outer face of a wall of a container for a fluid and along a propagation path for an elastic wave transmitted through the wall of the container wherein the elastic wave has a frequency of less than 5 kHz, more preferably less than about 2 kHz, and most preferably less than 1 kHz. A signal processor determines a change in a characteristic of the elastic wave between when a fluid is present in the container in the region of the propagation path and when a fluid is not present in the container in the region of the propagation path. One embodiment utilizes multiple horizontally oriented transmitting and receiving transducer pairs to detect levels of the fluid in the container. Another uses a vertically oriented transmitting and receiving transducer pair and the characteristic of the elastic wave is dependent upon the proportion of the propagation path along which the fluid is present in the container, thereby indicating the level of the fluid in the container. The detector may include a cross correlation detector for determining the change in the characteristics of the elastic wave, the elastic wave preferably has a frequency of 1000 Hz or lower, and the elastic wave characteristic may be the propagation time of the elastic wave, the amplitude of the received elastic wave or the phase of the received elastic wave.

9 Claims, 9 Drawing Sheets

NON-INVASIVE LOW FREQUENCY ELASTIC WAVE FLUID LEVEL SENSING SYSTEM FOR SLUDGE LADEN ENVIRONMENTS

This invention was made with Government support under contract No. 001 67-95-C0014 awarded by the Naval Undersea Warfare Center, Carderock Division. The Government has certain rights in this invention.

FIELD OF THE INVENTION

The present invention relates to a system for determining fluid levels and, in particular, to a non-invasive system for determining fluid levels in environments that are highly contaminated or laden with sludge or similar substances having physical properties similar to those of the fluids being sensed.

BACKGROUND OF THE INVENTION

There are many industrial and environmental processes and industries that require the storage or holding of fluids in various forms of containers or tanks for varying periods of time, from minutes to months or years. Typical examples would include oil storage tanks, sewage holding and treatment tanks, and processing and storage tanks as used, for example, in paper manufacturing and other chemical processes.

A common requirement in such holding and storage tanks is that of sensing or measuring the level of fluid in the tanks, for example, to warn when a tank is full or should be filled, to control the pumping of fluid into or from a tank so as to avoid overflow or pump damage when a tank is empty, and to otherwise control or measure the level of fluid in a tank. A recurring problem with sensing or measuring the level of fluid in a tank or other form of container, however, is that many of the fluids contain or are comprised of substances that leave or form deposits on the inner surfaces of the tanks that interfere or prevent the measurement or detection of the fluid levels. Such deposits, referred to hereafter as "sludge", may be comprised of solids dissolved or suspended in the fluids or components of the fluids themselves and typical examples would include the solid and semi-solid or semi-liquid components of sewage, components of petroleum products, the fibrous components of paper "slurry", and chemical and mineral deposits, such as "scale".

The effects of sludge buildup on fluid level sensing devices that were mounted internally to a tank were recognized and, although still used at the cost of frequent repair and cleaning, often under hazardous conditions, are still used. More recent developments, however, have been directed at externally mounted sensors that sense or measure some property of a tank that changes dependent upon the level of fluid therein. A typical example of such is described in U.S. Pat. Ser. No. 5,456,114 to Liu et al. for an ELASTIC WAVE SENSING SYSTEM, hereafter referred to as "Liu", which uses a transmitting transducer and a receiving transducer mounted on the outside of a tank wall to propagate a relatively high frequency elastic wave through the wall of the tank. The speed of propagation of the elastic wave through the wall of the tank is affected by whether there is fluid present against the inner wall of the tank along the propagation path and the change in time of propagation of the wave between the transmitting and receiving transducers is measured by a zero crossing technique to determine whether fluid is in contact with the inner wall of the tank along the propagation path. One implementation of this approach has been as a yes/no level detector using two closely spaced transducers, optionally with an associated "calibration" path comprised of a small container of water positioned as a parallel path between the transducers, to sense the presence or absence of fluid in the tank at the level of the transducers. Another implementation has placed one transducer at the bottom of the tank wall the other at the top of the tank wall and measured the change in propagation time between the transducers as an indicator of the proportion of the path between the transducers having fluid against the inner wall of the tank.

This method as taught by Liu uses an elastic wave signal in the frequency range of 5 to 25 kHz, typically at 12.5 kHz, and has been found to perform satisfactorily in situations where the inner surfaces of the tank are relatively clean of sludge or other deposits, such as large storage tanks for "clean" oil, such as heating or diesel oil. It has been found, however, that this method is not satisfactory in situations wherein a layer of "sludge" forms or is deposited on the inner wall of a tank or container along the propagation path of the elastic wave. For example, many ships are provided with sewage storage tanks for holding waste, thereby avoiding the necessity of frequent or continuous dumping of sewage into the surrounding waters and allowing the sewage to be disposed of in more environmentally acceptable ways. It has been found, however, that the inner walls of such tanks are typically covered with one to two inch thick layers of sludge comprised of solid, semi-solid and semi-liquid substances, usually saturated with water, and having density on the same order as that of the fluid held in the tank. It has also been found that a layer of such sludge having a thickness of even one eighth of an inch will appear to a fluid sensing detection system as embodied by Liu et al. to be the fluid that the system is trying to detect, thereby resulting in false or erroneous readings or indications of fluid levels.

The present invention provides a solution to these and other problems of the prior art.

SUMMARY OF THE INVENTION

The present invention is directed to a non-invasive elastic wave fluid level sensing system for use in sludge laden environments. The system includes a transmitting transducer mounted on an outer face of a wall of a container for a fluid and a receiving transducer mounted on the outer face of the wall of the container, the transmitting and receiving transducers being mounted along a propagation path for an elastic wave extending through the wall of the container between the transmitting transducer and the receiving transducer. A signal generator is connected to the transmitting transducer for driving the transmitting transducer to transmit an elastic wave through the wall and along the propagation path to the receiving transducer wherein the elastic wave has a frequency of less than one kHz. A signal processor is connected from the signal generator and the receiving transducer for determining a characteristic of the elastic wave along the propagation path and determining the change in the elastic wave characteristic between when a fluid is present in the container in the region of the propagation path and when a fluid is not present in the container in the region of the propagation path.

In one embodiment, the system includes a plurality of fluid level detectors, each fluid level detector being mounted against the outer wall of the container at a selected level along the vertical height of the container. Each detector includes a transmitting transducer and a receiving transducer positioned along a horizontally oriented propagation path wherein each transmitting transducer is connected from the signal generator and each receiving transducer is connected to the signal processor. The signal processor is responsive to the transmission of elastic waves between the transmitting transducer and the receiving transducer of each fluid level detector for determining, for each fluid level detector, a characteristic of the elastic wave along the propagation path of the fluid level detector and determining, for each fluid level detector, a change in the elastic wave characteristic between when a fluid is present in the container in the region of the propagation path of the fluid level detector and when a fluid is not present in the container in the region of the propagation path of the fluid level detector.

In another embodiment, a transmitting transducer and a receiving transducer are positioned vertically with respect to one another along the wall of the container so that the propagation path passes along a vertical path through the wall of the container between the transmitting and receiving transducers. The characteristic of the elastic wave is dependent upon the proportion of the propagation path along which the fluid is present in the container and the signal processor is responsive to a change in the elastic wave characteristic dependent upon the proportion of the propagation path along which the fluid is present in the container for determining the proportion of the propagation path along which fluid is present in the container, thereby indicating the level of the fluid in the container.

In a further embodiment of the present invention, the signal processor includes a cross correlation detector for determining the change in the characteristics of the elastic wave along the propagation path as a function of both the degree of phase shift and the amplitude difference between a baseline signal representing the elastic wave under one condition (full or empty) and a second signal representing the received elastic wave under the present condition. In a presently preferred embodiment of the cross correlation detector, the cross correlation detector includes a signal memory for storing samples of the second signal representing the complete received elastic wave and a multiplier/adder for generating a value representing the cross correlation between the baseline signal representing the elastic wave under one condition and the second signal representing the received elastic wave under the present condition by multiplying and adding the stored samples of the second signal represented the received elastic wave and the baseline signal.

Finally, in presently preferred embodiments of the present invention, the elastic wave has a frequency of 1000 Hz or lower, and the detected elastic wave characteristic may be the propagation time of the elastic wave, the amplitude of the received elastic wave or the phase of the received elastic wave.

DESCRIPTION OF THE DRAWINGS

The foregoing and other objects, features and advantages of the present invention will be apparent from the following description of the invention and embodiments thereof, as illustrated in the accompanying figures, wherein.

DESCRIPTION OF A PRESENTLY PREFERRED EMBODIMENT

Figure 1:
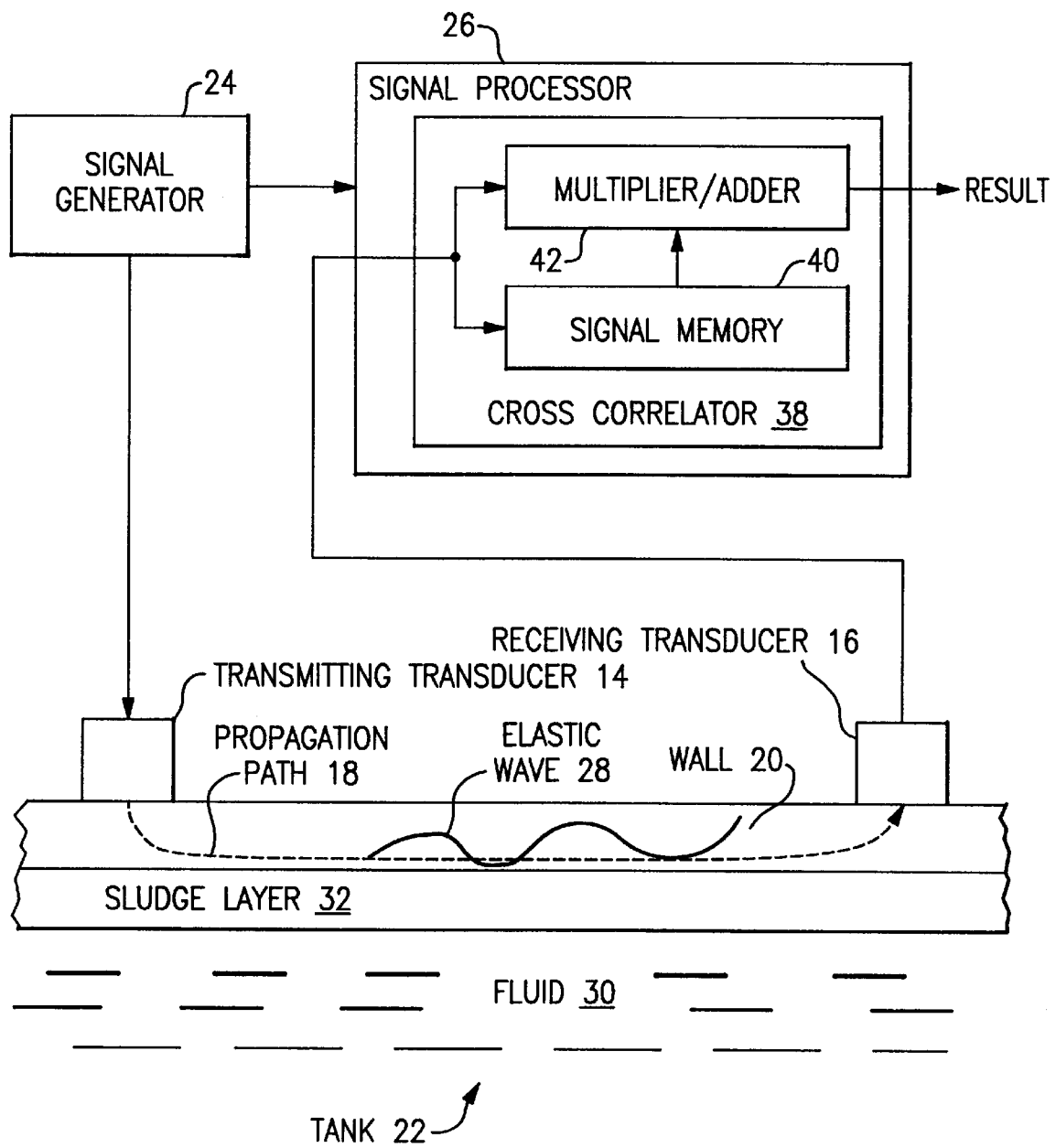
FIG. 1 is an illustrative cross section diagram of a fluid level detection system.
Figure 2:
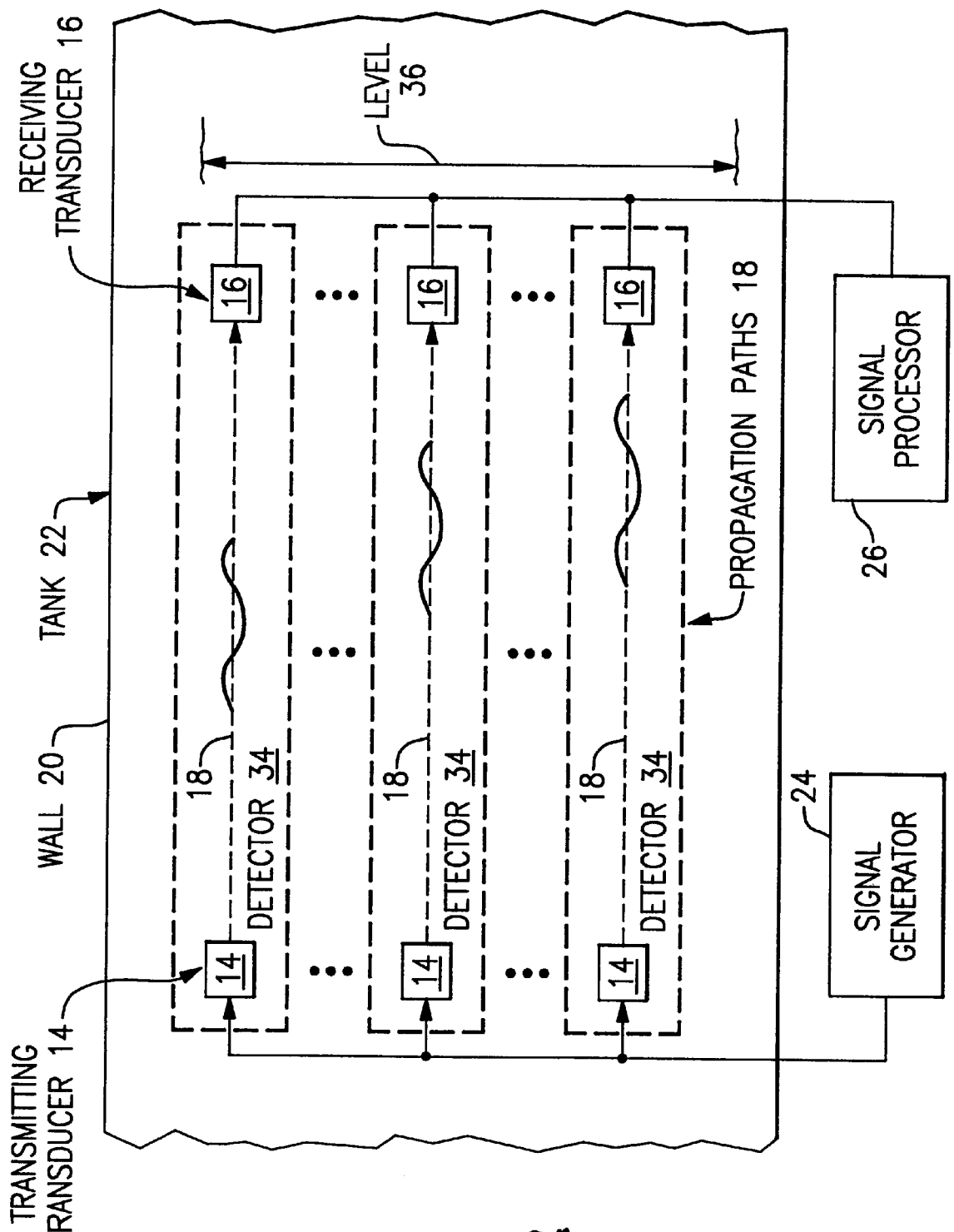
FIG. 2 is an illustrative diagram of a fluid level detection system having multiple transducer pairs.
Figure 3:
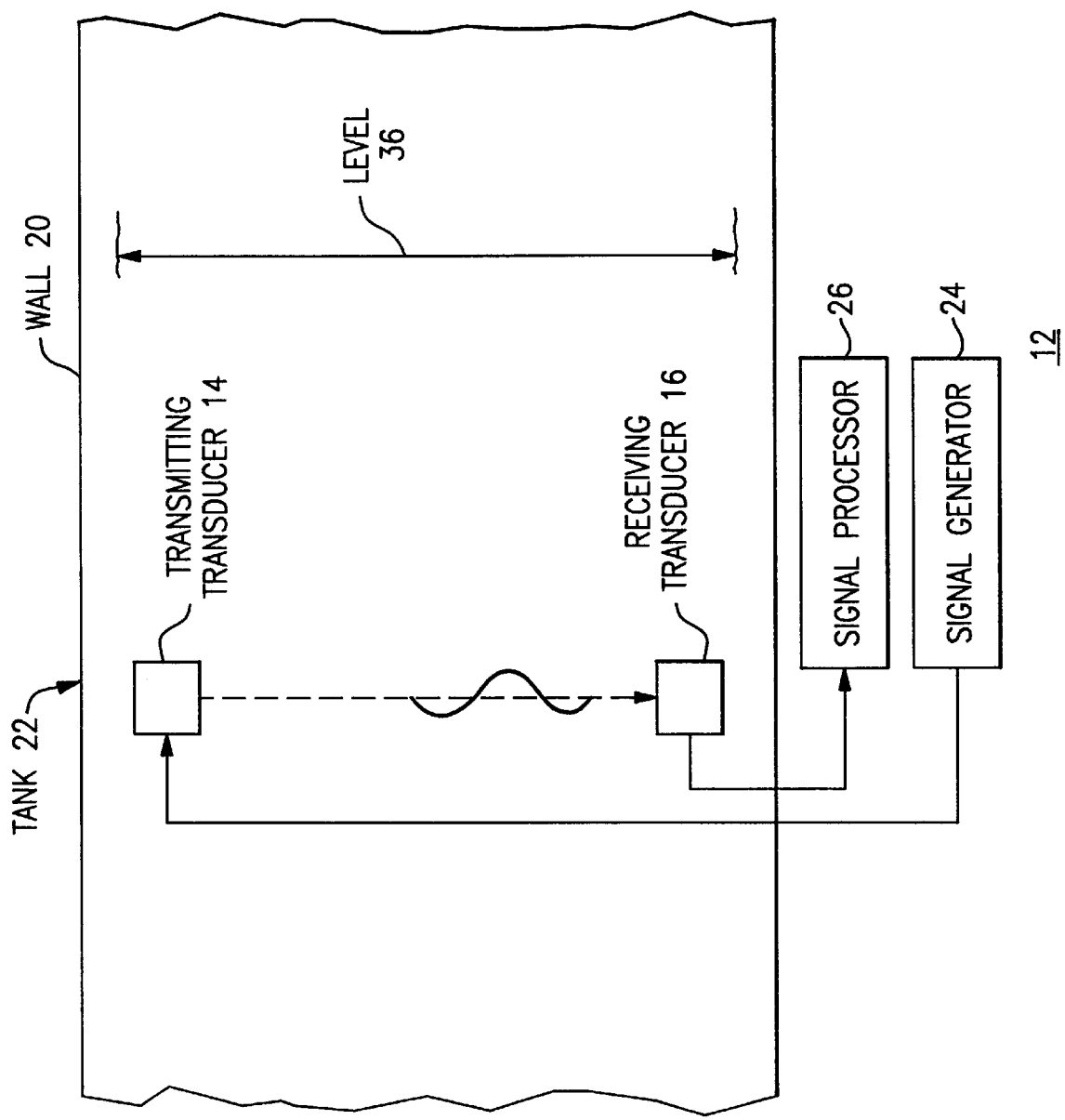
FIG. 3 is an illustrative diagram of a fluid level measurement system.

Referring to FIGS. 1, 2 and 3, therein are shown illustrative diagrams of a Fluid Level Detection System 10 and a Fluid Level Measurement System 12 according to the present invention. As will be described below, the system of the present invention operates according to the well known principle described, for example, in U.S. Pat. Ser. No. 5,456,114 to Liu et al. for an ELASTIC WAVE SENSING SYSTEM, that the propagation velocity of an elastic or flexural wave in a wall is dependent upon the loading, as by a fluid, on one or both faces of the wall.

As represented in FIG. 1, which shows a cross sectional view of a single fluid detector of the present invention, each of Fluid Level Detection System 10 and Fluid Level Measurement System 12 includes at least one Transmitting Transducer 14 and at leastone corresponding Receiving Transducer 16 affixed to the outer face of a Wall 20 of a Tank 22 and located at opposite ends of a Propagation Path 18 passing through a Wall 20 of a Tank 22, a Signal Generator 24 connected to each Transmitting Transducer 14 and a Signal Processor 26 connected from the Signal Generator 24 and from each Receiving Transducer 16. As will be described further below, the propagation time of an Elastic Wave 28 along Propagation Path 18 between Transmitting Transducer 14 and Receiving Transducer 16 is affected by and dependent upon whether a Fluid 30 is present against the inner face of Wall 20 in the region of Propagation Path 18, thereby structurally "loading" Wall 20. As will also be discussed below, the structural "loading" of Wall 20 is also affected by the possible presence of a Sludge Layer 32 on the inner face of Wall 20 in the region of Propagation Path 18.

As illustrated in FIG. 2, which represents a side view of a tank provided with a fluid level detection system according to the present invention, the present invention may be embodied or implemented in a Fluid Level Detection System 10 comprised of one or more Fluid Level Detectors 34, each including a Transmitting Transducer 14 and a corresponding Receiving Transducer 16 communicating across a Propagation Path 18, wherein each Fluid Level Detector 28 detects the presence or absence of Fluid 30 in Tank 22 at or above a Level 36 at which a Fluid Level Detector 34 is affixed to the outer side of Wall 20. As will be described further below, the propagation time of an elastic wave, also referred to as a flexural wave, through Wall 20 and between Transmitting Transducer 14 and Receiving Transducer 16 along Propagation Path 18 is dependent upon whether Fluid 30 is present against the inner face of Wall 20 in the region at or above the Propagation Path 18. As such, the presence or absence of Fluid 30 against the inner face of Wall 20 in the region of a Propagation Path 18, and thereby whether Fluid 30 is at or above a Level 36 of the Propagation Path 18, may be determined by measuring the propagation time between the Transmitting Transducer 14 and the Receiving Transducer 16 along the Propagation Path 18. In general, the Transmitting Transducer 14 and Receiving Transducer 16 of each Fluid Level Detector 34 are generally located along a horizontal line at the selected fluid level detection height from the bottom of Tank 22 and so that their Propagation Path 18 is similarly horizontal, that is, parallel to the surface of Fluid 32. In general, and in the presently preferred embodiment, Transmitting Transducer 14 and Receiving Transducer 16 are located essentially adjacent one another. In other embodiments, Transmitting Transducer 14 and Receiving Transducer 16 may be spaced so that Propagation Path is, for example, a few inches or foot or two long, and it is possible that in some embodiments Transmitting Transducer 14 and Receiving Transducer 16 may be spaced even farther apart.

The present invention may also be implemented or embodied in a Fluid Level Measurement System 12 as shown in FIG. 3, which is a side view of a fluid level measurement system. As shown in FIG. 3, a Fluid Level Measurement System 12 is generally comprised of a single Transmitting Transducer 14 and a single Receiving Transducer 16 that are positioned vertically with respect to one another so that the Propagation Path 18 between Transmitting Transducer 14 and Receiving Transducer 16 generally extends along at least the entire range of Levels 36 of interest of Fluid 30. The propagation time of an elastic wave between Transmitting Transducer 14 and Receiving Transducer 16 along Propagation Path 18 will be dependent upon the proportion of Propagation Path 18 wherein Fluid 30 is present against the inner face of Wall 20 relative to the proportion of Propagation Path 18 wherein Fluid 30 is not present against the inner face of Wall 20. It will be noted that in alternate embodiments of this system, the positions of Transmitting Transducer 14 and Receiving Transducer 16 may be reversed from those shown in FIG. 3, and that a single Transmitting Transducer 14 may be used with multiple Receiving Transducers 16, for example, with the Transmitting Transducer 14 located at a mid-point of a vertical chain of two or more Receiving Transducers 16.

Figure 4:
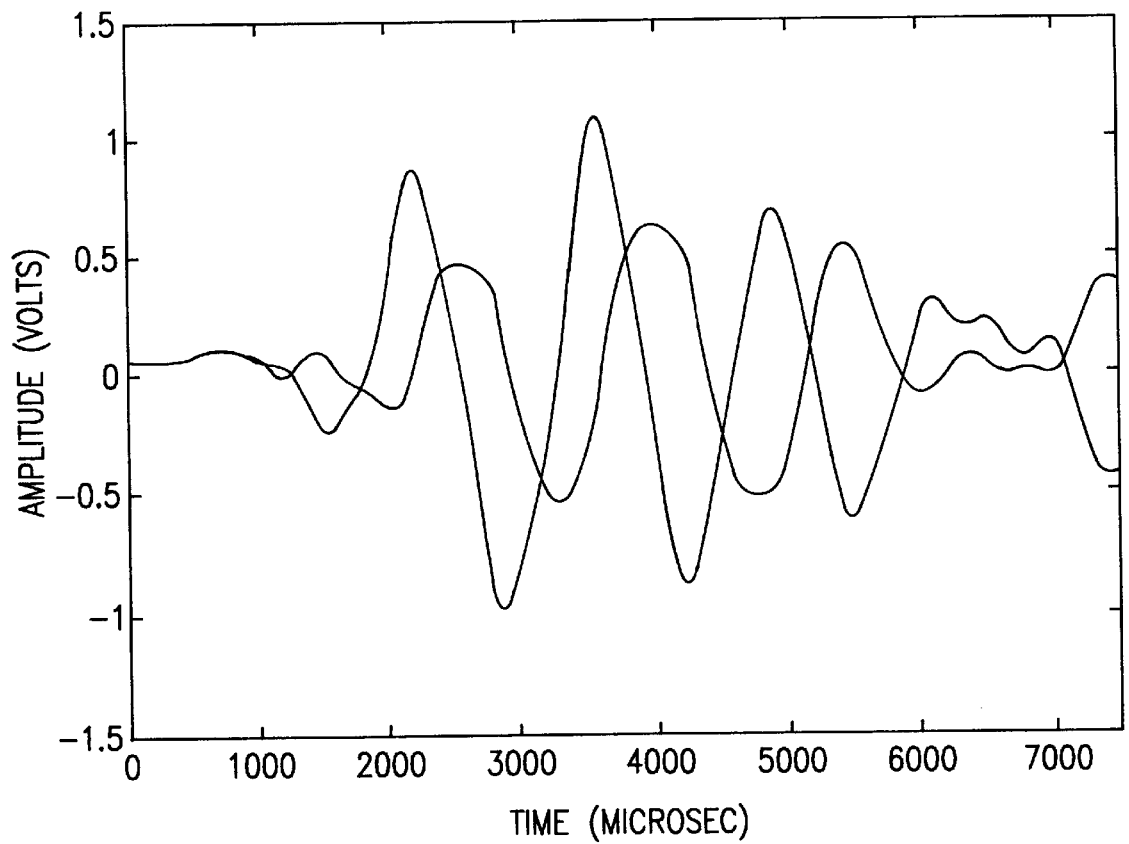
FIG. 4 is an illustration of the propagation time of an elastic wave in the wall of a tank with and without fluid behind the source-receiver pair.
Figure 5:
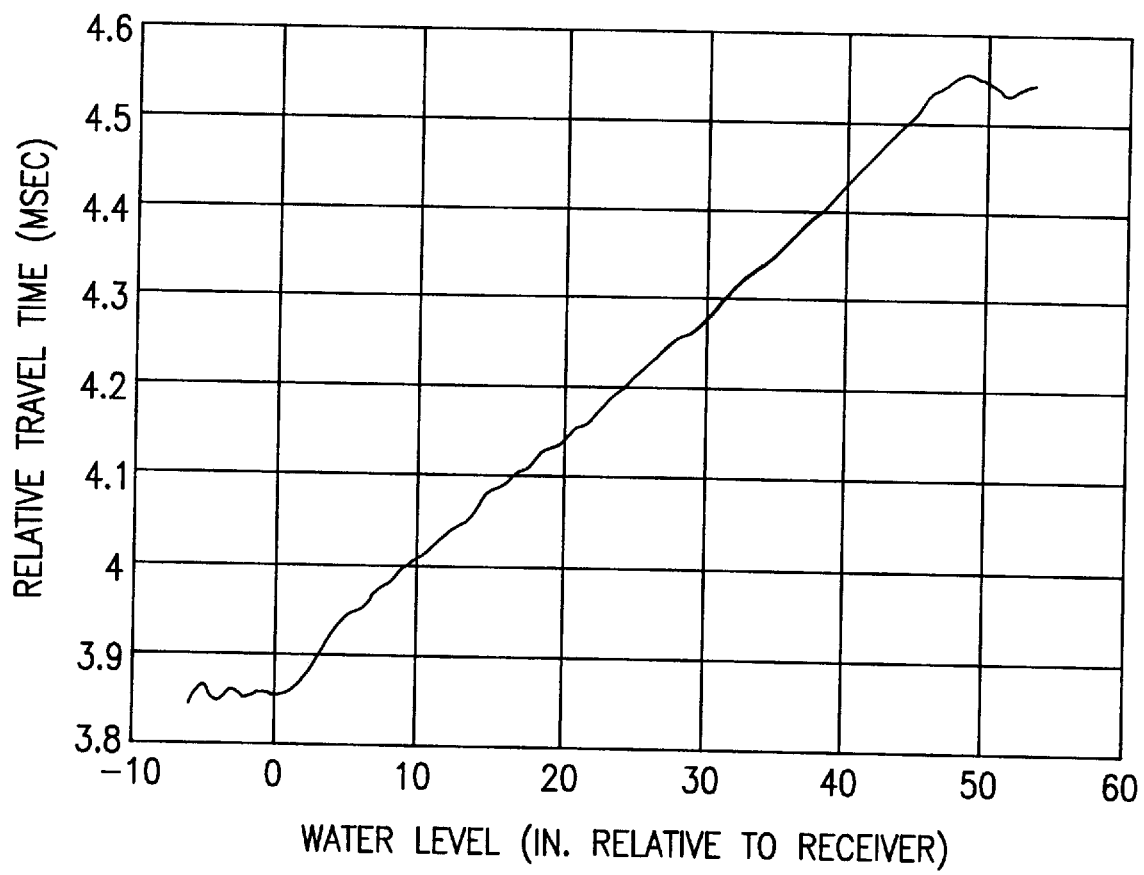
FIG. 5 is an illustration of the change in propagation time of an elastic wave for a fluid level measurement system.

The change in propagation time of an elastic wave along a Propagation Path 18 in a Wall 20 of a Tank 22 is illustrated in FIG. 4, which shows measurements made of the propagation times of an approximately 750 Hz elastic wave along a Propagation Path 18 having a length of 21 inches wherein a Fluid 30, specifically water, is present and not present against the inner wall of the Tank 22 along Propagation Path 18. The change in propagation time for a 750 Hz elastic wave for the configuration illustrated in FIG. 3, that is, for a continuous level measurement along a Propagation Path 18 extending 4 feet vertically along the side of a 7 feet deep Tank 22, is illustrated in FIG. 5. It will be noted in FIG. 5 that the change in propagation time versus level of Fluid 30 is generally linear so long as the level of Fluid 30 is between the Transmitting Transducer 14 and the Receiving Transducer 16.

Considering an exemplary application of the present invention in illustration of the problems of the prior art addressed by the present invention, it is known that the propagation time of an elastic wave in the wall of a tank or other container is affected by the presence or absence of a relatively thin layer of fluid and that the thickness of the effective layer of fluid is dependent upon the thickness of the tank wall and the frequency of the elastic wave. For example, the propagation time of an elastic wave is changed significantly by a layer of fluid on the order of one to two inches in thickness for elastic waves in the frequency range of 5 kHz to 25 kHz and for typical tank wall thicknesses, which is why the frequency range of 5 kHz to 25 kHz is taught as preferable for typical applications of such systems.

In many applications, however, such as shipboard sewage holding tanks, sewage processing tanks, and many industrial processes, significant thicknesses of "sludge", represented above as Sludge Layer 32, form or are deposited on the inner wall of a tank or container along the propagation path of the elastic wave. The inner surfaces of such tanks are often laden with layers of sludge up to one to two inches in thickness wherein the sludge, because of its composition, is approximately of the same density as the fluid to be detected or measured, so that the layer of sludge "loads" the tank wall in much the same manner as a fluid. Because the effective thickness of the "loading" layer in terms of affecting the velocity of propagation of an elastic wave in the usual range of frequencies is on the same order or even less than the thickness of the sludge layer, the sludge layer masks or significantly reduces the loading effects of the fluid to be detected. As a consequence, the presence of the sludge layer results in false or erroneous measurements of the elastic wave propagation time.

Figure 6:
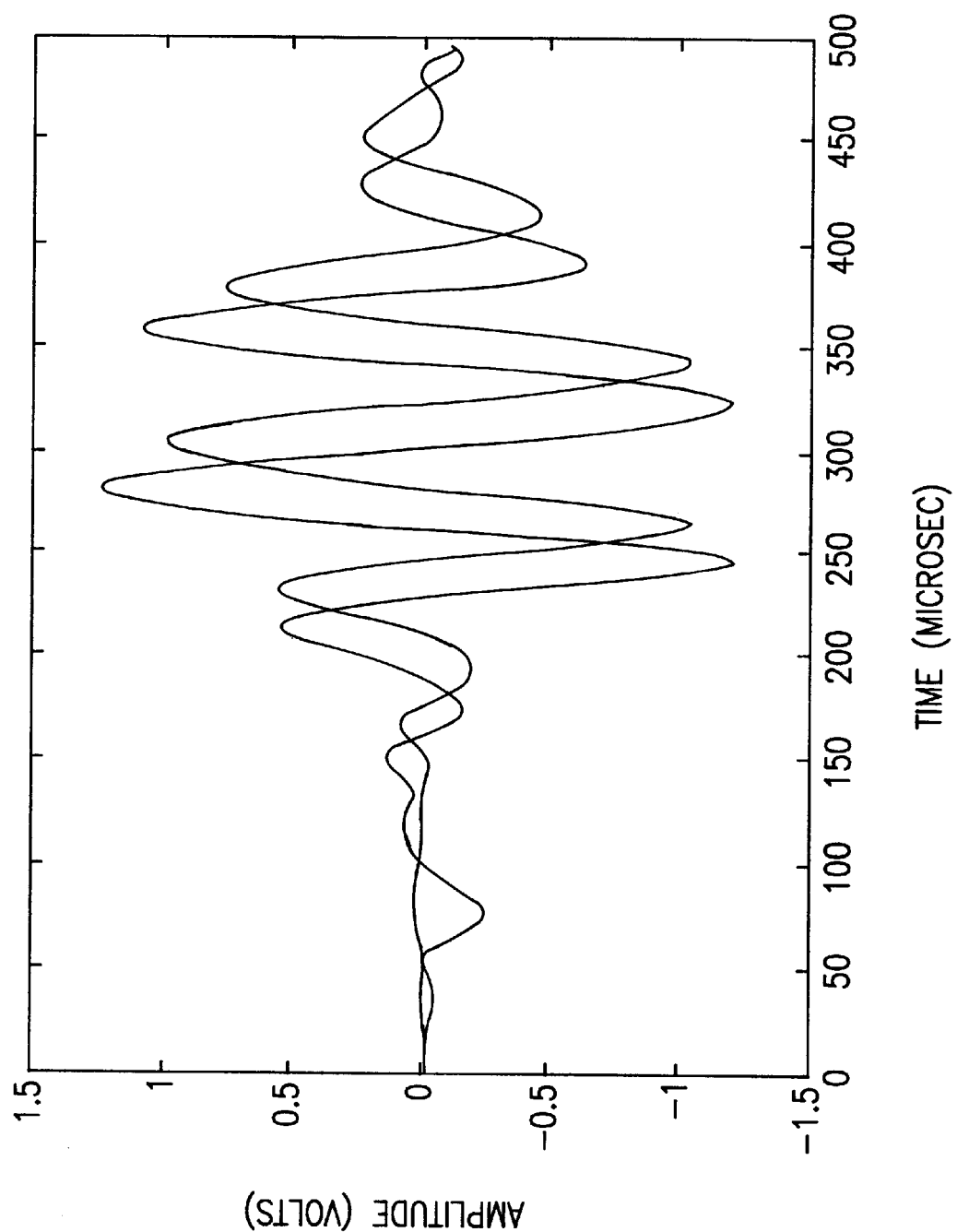
FIGS. 6 and 7 illustrate the change in propagation time of an elastic wave without and without a layer of sludge.
Figure 7:
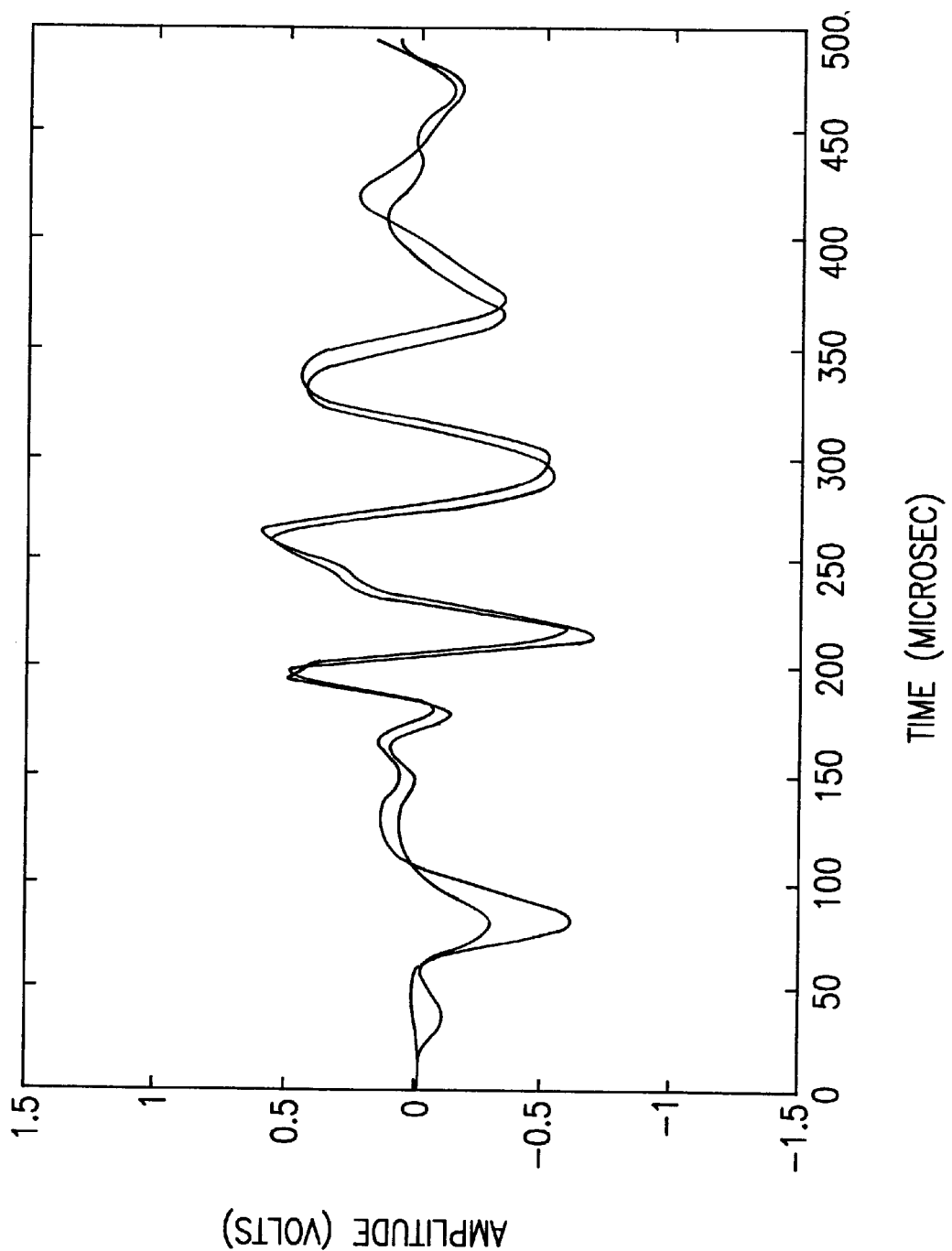

To consider a specific example, it has been found that in a sewage holding tank the inner walls of the tank are often covered with layers of sludge of an eighth of an inch or more, and frequently up to one or two inches or more, as described above, wherein the layers of sludge are of approximately the same density as the fluid held in the tank. It is known, and can be shown, that in order for a layer of fluid bearing against the wall of a tank to "load" the wall to affect the propagation velocity of an elastic wave in the wall, the thickness of the fluid layer must be greater than ¼ wavelength of the elastic wave. In a typical application, wherein the steel plate wall of a tank is ¼ inch thick and the elastic wave is transmitted at a frequency of 12 kHz, that is, in the frequency range taught by the prior art, the wavelength of the elastic wave is approximately 2.5 inches, so that the ¼ wavelength of the wave is 0.625 inches. As such, a fluid layer of 0.625 inches will "load" the wall of the tank to detectably affect the propagation velocity of the elastic wave. Unfortunately, a sludge layer of no more than 0.625 inches will also "load" the wall to produce the same affect on the elastic wave and, because loading layer thicknesses of greater than 0.625 inches, that is, ¼ wavelength of the elastic wave, have a significantly reduced effect of the propagation velocity of the elastic wave, any additional loading by the fluid will be masked by the sludge layer. This affect is illustrated in FIGS. 6 and 7, which respectively show the difference in elastic wave propagation velocity of the presence and absence of a fluid loading layer without and with a "sludge" loading layer having a thickness of 1 inch and an elastic wave frequency of 12 kHz. It can be seen from FIGS. 6 and 7 that the loading effect of a sludge layer of moderate thickness is sufficient to severely degrade the ability of a high frequency elastic wave system, that is, operating at 5 kHz to 25 kHz, to detect the presence or absence of the fluid to be detected.

According to the present invention, the effects of sludge layers in elastic wave wall loading fluid detection systems can be significantly reduced, and satisfactory performance can be achieved, by reducing the frequency and thus the ¼ wavelength of the elastic wave to a frequency of less than 5 kHz, more preferably less than about 2 kHz and most preferably less than 1 kHz. For example, an elastic wave at a frequency of 1 kHz will have a wavelength of approximately 8 inches and a ¼ wavelength of approximately 2 inches, so that the system will detect and measure the effects of fluid loading on the wall of a tank for sludge layer thicknesses of less than approximately 2 inches. In as much as the typical maximum thickness of sludge layer found in many applications is 2 inches or less, a frequency of lower than 1 kHz, such as 750 Hz, will "look though" the sludge layer to detect the loading effect of a fluid layer outside the sludge layer. In applications wherein the sludge layer is greater than 2 inches, the frequency of the elastic wave may be decreased proportionally.

Figure 8:
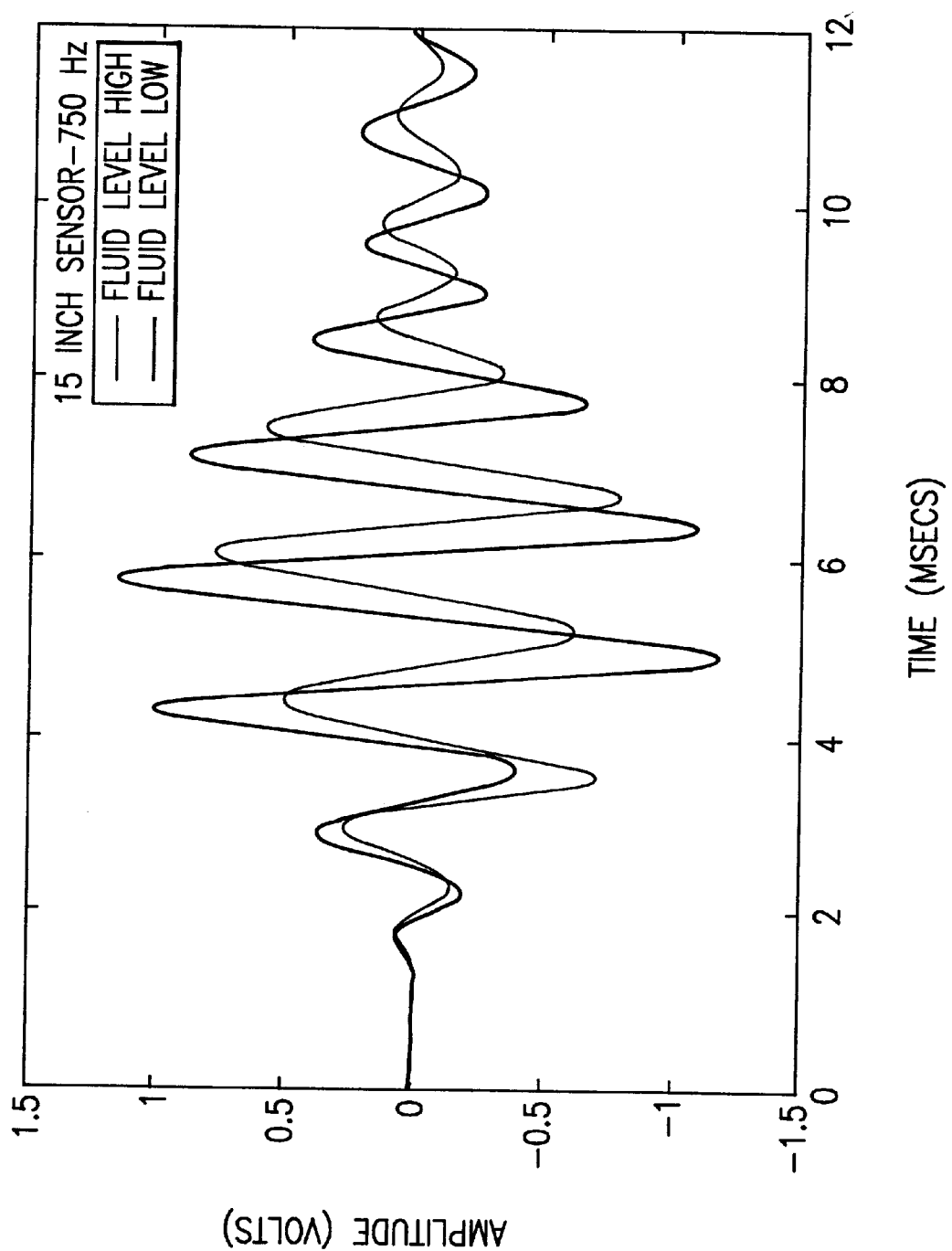
FIGS. 8 and 9 illustrate the change in propagation time of an elastic wave over a horizontal propagation path with a layer of sludge or an actual shipboard sewage tank.
Figure 9:
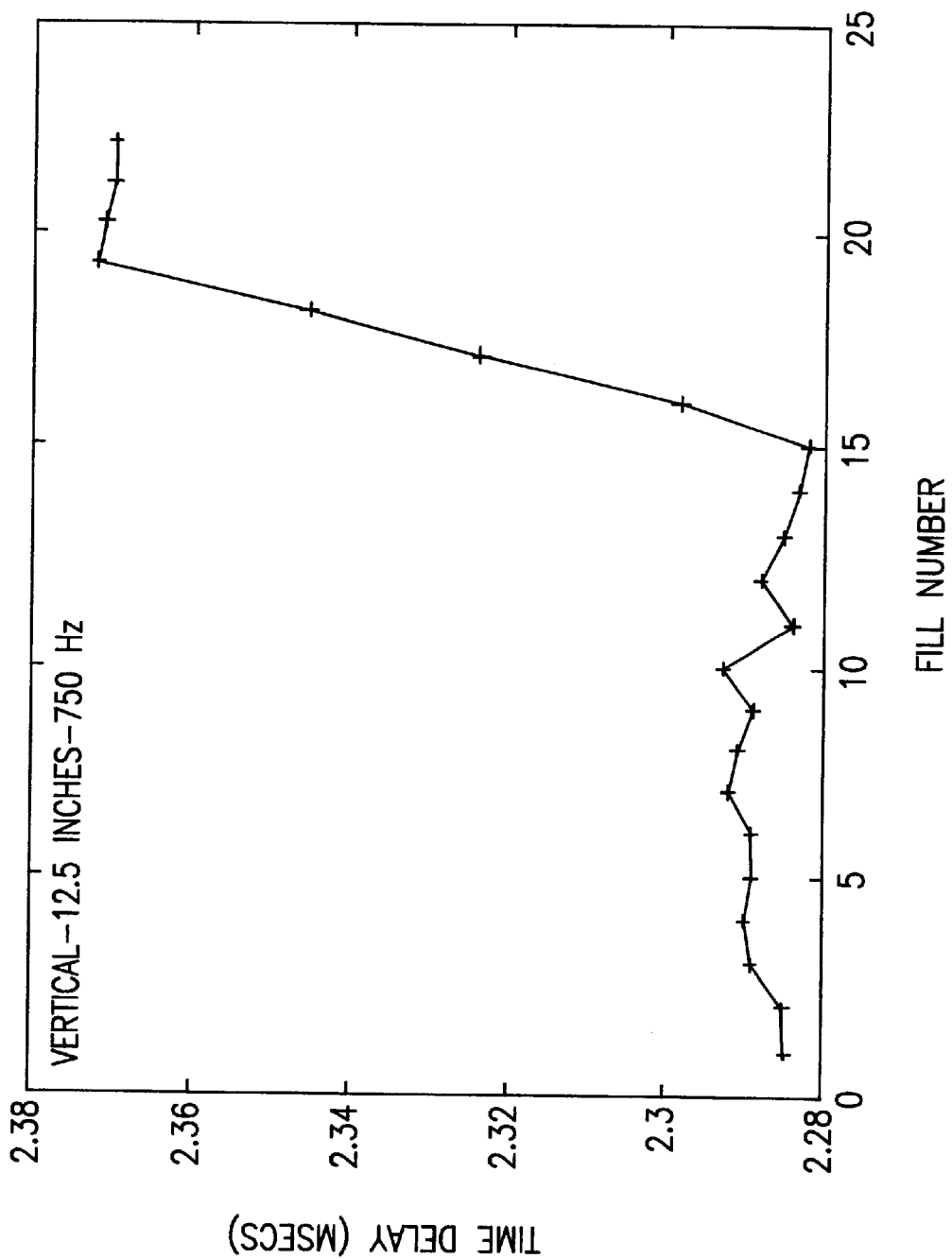

The operation of the present invention is illustrated in FIGS. 8 and 9 for an implementation of the present invention using a Ling Model 207 Shaker as a Transmitting Transducer 14 and an accelerometer, such as a Model AMP01, as a Receiving Transducer 16. FIG. 8 shows the shift in propagation time for a shift in fluid level for a one inch layer of sludge over a horizontal propagation path of 15 inches and an elastic wave having a frequency of 750 Hz. FIG. 9 illustrates the case of a vertical propagation path of 12.5 inches, an elastic wave at 750 Hz and one inch of sludge as the fluid level rises from the lower to the upper transducer, wherein the filling of the tank is represented in FIG. 9 as "Fill Numbers" representing equal increments of fluid introduced into the tank.

It may be seen from both FIG. 8 and 9 that the performance of a low frequency elastic wave wall loading fluid detection systems is significantly improved over that of a high frequency system in highly sludge laden environments.

In another aspect of the present invention, it must be noted that the high frequency elastic wave wall loading fluid detection systems typical of the prior art detect the shift in propagation time of the elastic wave by sampling the received waveform and detecting the shift in time of the zero crossing point of the waveform due to fluid loading of the wall of the container. It has been found, however, that this zero crossing detection method is less satisfactory at lower frequencies as used in the low frequency elastic wave wall loading fluid detection system of the present invention because of possible false signals or indications arising from the greater propagation characteristics of the lower frequency signals. For example, such false signals or interactions may arise from interactions between sensors in multi-sensor systems, possible reflections of the elastic wave through the structure of the tank, including the structures surrounding the tank, possible interactions with noise from other sources in the structures, and possible reflections through the fluid in the tank., at certain fluid levels relative to the propagation path the zero crossing point may reverse its direction of shift. By way of example, in the instance of a level detection system as exemplified by Fluid Level Detection System 10, it was found that at certain fluid levels relative to the propagation path of a transducer pair the zero crossing point would appear to reverse its direction of shift as the fluid level increased past a certain point above the transducer pair.

As a consequence, and as indicated in FIG. 1, the zero crossing detection method of the prior art was replaced in Signal Processor 26 by a Cross Correlator 38 for cross correlation detection between the received elastic wave and a baseline elastic wave, which in the presently preferred embodiment is generated by using Fluid Level Detection System 10 to transmit, receive and store in Cross Correlator 38 an elastic wave under known initial conditions, such as when the fluid is at a known level. Cross Correlator 38 then determines the time of propagation of an elastic wave along the propagation path as a function of both the degree of phase or time shift between the signals and the amount of sample by sample amplitude difference between the signals, as represented by the resemblance, or cross correlation, between the received and baseline waves. As indicated, Cross Correlator 38 includes a Signal Memory 40 for storing samples of the complete received elastic wave and a Multiplier/Adder 42 for generating a value represented the resemblance, or cross correlation, between the received and baseline signals by multiplying and adding the stored samples of the received elastic wave and a baseline transmitted elastic wave from Signal Generator 24. As the design and operation of such cross correlators is well known to those of ordinary skill in the arts, Cross Correlator 38 will not be described further.

Lastly, the above discussions and description of a Fluid Level Detection System 10 have described the system as detecting the presence of absence of fluid against the inner wall of a tank, or the level of the fluid in the tank, by detecting the shift in the propagation time of the elastic wave. it will be recognized by those of ordinary skill in the arts, however, that the propagation impedance of a tank is a complex function wherein the presence or absence of a fluid along the elastic wave propagation path will appear as changes in the propagation time of the elastic wave, the amplitude of the received signal, and the phase of the received signal relative to a baseline wave. It will thus be recognized by those of ordinary skill in the relevant arts that any of these characteristics of the elastic wave, or any combination of these characteristics of the elastic wave, may be used to detect the presence or absence or the level of a fluid in a tank and the means by which the presently described embodiment may be adapted to use any of these characteristics of the elastic wave will be apparent to those of ordinary skill in the relevant arts.

Finally, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. Therefore, it is the object of the appended claims to cover all such variation and modifications of the invention as come within the true spirit and scope of the invention.

What is claimed is:

1. A non-invasive elastic wave fluid level sensing system for use in sludge laden environments, comprising:

a transmitting transducer mounted on an outer face of a wall of a container for a fluid wherein the fluid is of a nature to deposit a layer of sludge on an inner face of the wall of the container and wherein the effect of the layer of sludge on the inner face of the wall of the container on the propagation of an elastic wave through the wall of the container is similar to the effect of a presence of the fluid on the inner face of the wall of the container, a receiving transducer mounted on the outer face of the wall of the container along a propagation path for an elastic wave extending through the wall of the container and between the transmitting transducer and the receiving transducer, a signal generator connected to the transmitting transducer for driving the transmitting transducer to transmit an elastic wave through the wall and along the propagation path to the receiving transducer, the elastic wave having a frequency of less than one kHz, and a signal processor connected from the signal generator and the receiving transducer for determining a characteristic of the elastic wave along the propagation path and determining a change in the elastic wave characteristic between when a fluid is present in the container in the region of the propagation path and when a fluid is not present in the container in the region of the propagation path, and wherein the signal processor further comprises a cross-correlation detector for determining a cross-correlation detector for determining the change in the elastic wave characteristic as a function of both the degree of phase shift and the amount of amplitude difference between a stored baseline signal representing the received elastic wave with the tank fluid level at one state and a second (and a second)signal representing the received elastic wave with the tank fluid level at a changed state.

2. The non-invasive elastic wave fluid level sensing system for use in sludge laden environments of claim 1, wherein the cross correlation detector includes:

a signal memory for storing samples of the second signal representing the complete received elastic wave and a multiplier/adder for generating a value represented the cross correlation between the baseline signal representing the received elastic wave in the one state of the tank level and the second signal representing the received elastic wave by multiplying and adding the stored samples of the second signal represented the current received elastic wave and the baseline signal.

3. The non-invasive elastic wave fluid level sensing system for use in sludge laden environments of claim 1, further comprising:

a plurality of fluid level detectors, each fluid level detector being mounted against the outer wall of the container at a selected level along the vertical height of the container and including a transmitting transducer and a receiving transducer positioned along a horizontally oriented propagation path, the transmitting transducer being connected from the signal generator and a receiving transducer connected to the signal processor, the signal processor being responsive to the transmission of elastic waves between the transmitting transducer and the receiving transducer of each fluid level detector for determining, for each fluid level detector, the characteristic of the elastic wave along the propagation path of the fluid level detector and determining, for each fluid level detector, the change in the elastic wave characteristic between when a fluid is present in the container in the region of the propagation path of the fluid level detector and when a fluid is not present in the container in the region of the propagation path of the fluid level detector.

4. The non-invasive elastic wave fluid level sensing system for use in sludge laden environments of claim 1, wherein:

the transmitting transducer and the receiving transducer are positioned vertically with respect to one another along the wall of the container so that the propagation path passes along a vertical path through the wall of the container between the transmitting and receiving transducers, wherein the characteristic of the elastic wave is dependent upon the proportion of the propagation path along which the fluid is present in the container, and the signal processor is responsive to the change in the elastic wave characteristic dependent upon the proportion of the propagation path along which the fluid is present in the container for determining the proportion of the propagation path along which fluid is present in the container, thereby indicating the level of the fluid in the container.

5. The non-invasive elastic wave fluid level sensing system for use in sludge laden environments of claim 1 wherein the elastic wave characteristic is the propagation time of the elastic wave between the transmitting and receiving transducers.

6. The non-invasive elastic wave fluid level sensing system for use in sludge laden environments of claim 1 wherein the elastic wave characteristic is the amplitude of the received elastic wave.

7. The non-invasive elastic wave fluid level sensing system for use in sludge laden environments of claim 1 wherein the elastic wave characteristic is the phase of the received elastic wave.

8. A non-invasive elastic wave fluid level sensing system for use in sludge laden environments, comprising:

a transmitting transducer mounted on an outer face of a wall of a container for a fluid, a receiving transducer mounted on the outer face of the wall of the container along a propagation path for an elastic wave extending through the wall of the container and between the transmitting transducer and the receiving transducer, a signal generator connected to the transmitting transducer for driving the transmitting transducer to transmit an elastic wave through the wall and along the propagation path to the receiving transducer, the elastic wave having a frequency of less than two kHz, and a signal processor connected from the signal generator and the receiving transducer for determining a characteristic of the elastic wave along the propagation path and determining a change in the elastic wave characteristic between when a fluid is present in the container in the region of the propagation path and when a fluid is not present in the container in the region of the propagation path;

wherein the signal processore further comprises a cross-correlation detector for determining the change in the elastic wave characteristic as a function of both the degree of Phase shift and the amount of amplitude difference between a stored baseline signal representing the received elastic wave with the tank fluid level at one state and a second signal representing the received elastic wave with the tank fluid level at a changed state.

9. A non-invasive elastic wave fluid level sensing system for use in sludge laden environments, comprising:

a transmitting transducer mounted on an outer face of a wall of a container for a fluid, a receiving transducer mounted on the outer face of the wall of the container along a propagation path for an elastic wave extending through the wall of the container and between the transmitting transducer and the receiving transducer, a signal generator connected to the transmitting transducer for driving the transmitting transducer to transmit an elastic wave through the wall and along the propagation path to the receiving transducer, the elastic wave having a frequency of less than five kHz, and a signal processor connected from the signal generator and the receiving transducer for determining a characteristic of the elastic wave along the propagation path and determining a change in the elastic wave characteristic between when a fluid is present in the container in the region of the propagation path and when a fluid is not present in the container in the region of the propagation path;

wherein the signal processor further comprises a cross-correlation detector for determining the change in the elastic wave characteristic as a function of both the degree of phase shift and the amount of amplitude difference between a stored baseline signal representing the received elastic wave with the tank fluid level at one state and a second signal representing the received elastic wave with the tank fluid level at a changed state.

* * * * *